United States Patent [19]

Liang

[11] 4,181,670

[45] Jan. 1, 1980

[54] PHENYL 5Z,8Z,11Z,14Z-EICOSATETRAENOATE AND

[75] Inventor: Chi-Dean Liang, Glenview, Ill.

[73] Assignee: G. D. Searle & Co., Skokie, Ill.

[21] Appl. No.: 968,339

[22] Filed: Dec. 11, 1978

[51] Int. Cl.² .......................... C09F 5/08; C09F 7/10; C11C 3/00
[52] U.S. Cl. ................................ 260/410.5; 424/312; 424/314
[58] Field of Search ...................................... 260/410.5

[56] References Cited

U.S. PATENT DOCUMENTS

| 3,972,907 | 8/1976 | Baran et al. | 260/410.9 R |
| 4,124,612 | 11/1978 | Peterson | 260/410.5 |

OTHER PUBLICATIONS

Lancet 2, pp. 117–119 (1978).
The Merck Index, 9th Ed., p. 793.

*Primary Examiner*—John F. Niebling
*Attorney, Agent, or Firm*—James R. Henes; John M. Brown

[57] ABSTRACT

Preparation and use of platelet aggregation inhibiting and antisecretory phenyl 5Z,8Z,11Z,14Z-eicosatetraenoate and congeners are disclosed.

10 Claims, No Drawings

PHENYL 5Z,8Z,11Z,14Z-EICOSATETRAENOATE AND CONGENERS

This invention relates to phenyl 5Z,8Z,11Z,14Z-eicosatetraenoate and congeners, and to processes for the preparation thereof. More particularly, this invention provides new, pharmacologically useful, and unobvious chemical compounds of the formula

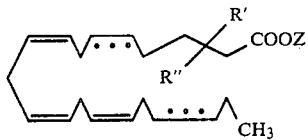

wherein R' represents hydrogen, 2-alkyl or 3-alkyl; R" represents hydrogen or 2-alkyl except when R' represents 3-alkyl, in which circumstance R' represents solely hydrogen; Z represents phenyl optionally substituted by 1 or more alkyls; and the dotted lines signify that a 5Z double bond or 5Z and 17Z double bonds can be present.

Among the alkyls represented by R' and R", those containing fewer than 3 carbons—i.e., methyl and ethyl—are preferred. Among the substituted phenyls represented by Z, those containing fewer than 4 alkyls each containing fewer than 5 carbons—i.e., methyl, ethyl, 1-methylethyl, 1,1-dimethylethyl, propyl, 1-methylpropyl, and butyl—are preferred. And among the variously-unsaturated eicosanoic acid esters of this invention, 5Z,8Z,11Z,14Z-tetraenoates are preferred.

The compounds to which this invention relates are useful by reason of their valuable pharmacological properties. Thus, for example, they are extraordinarily potent inhibitors of platelet aggregation. Further, they are antisecretory agents.

The platelet aggregation inhibitory potency of the instant compounds is evident from results of the following test procedure: Male Charles River COBS CD-1 retained breeder rats, 6-9 mos. of age and weighing 500-700 g apiece, are individually caged and maintained a standard rat diet puls water ad ligitum. Such animals are known to be characterized by spontaneous platelet aggregation [Saunders et al., Lab. Anim. Sci., 27, 757 (1977)]. The potency of a compund observed to induce inhibition of the aggregation is evaluated by (1) intragastrically administering to each of a group of 4 of the animals one of at least four appropriately different doses of compound dissolved or suspended in 1 ml/kg of an inert vehicle such as polyethylene glycol or water; (2) withdrawing from the inferior vena cava of each animal, 3 hrs. post medication, 1 ml of blood via each of two 5-ml polypropylene syringes equipped with 20-gauge needles and containing, respectively, 4 ml of buffered citrate/formalin and 4 ml of buffered citrate [See Saunders et al., loc cit., for composition.]; (3) separately mixing the contents of each syringe, transferring some to 15-ml siliconized centrifuge tubes, and maintaining the mixtures therein for 15 min. at 25° C.; (4) centrifuging for 14 min. at 170 g; (5) counting the number of platelets in each supernatant via a hemacytometer and 430X phase-contrast microscope; (6) determining the platelet aggregate ratio (PAR) for each dose in each animal by dividing the platelet count in the citrate/formalin supernatant by the platelet count in the citrate supernatant; and (7) plotting the mean PAR values as ordinates against the corresponding doses as abscissae, fitting a line thereto via the method of least squares, and reading therefrom the dose whereat the PAR is 0.85, a value which differs significantly ($P \leq 0.05$) from the PAR of $0.7478 + 0.0938$ for controls identically treated excepting that no compound is administered, and which thus characterizes the platelet inhibiting $ED_{50}$ of the compound tested. 4-(1,1-Dimethylethyl)phenyl 5Z,8Z,11Z,14Z-eicosatetraenoate and 4-(1,1-dimethylethyl)phenyl 2,2-dimethyl-5Z,8Z,11Z, 14Z-eicosatetraenate, the products of Examples 4 and 8 hereinafter were found to have $ED_{50}$'s of 1.1 and 2.28 mg/kg, respectively, when assayed via the foregoing procedure, whereas the $ED_{50}$'s of 5Z,8Z,11Z,14Z-eicosatetraenoic acid and 2,2-dimethyl-5Z,8Z,11Z,14Z-eicosatetraenoic acid were 18.2 and 13.2 mg/kg, respectively.

The antisecretory utility of the instant compounds is evident from the results of a standardized test carried out substantially as described in U.S. Pat. No. 3,690,904 wherein the aforesaid products of Examples 4 and 8 decreased acid output significantly ($P \leq 0.05$) when administered intragastrically at 25 and 50 mg/kg, respectively.

Results of tests set forth above are specified merely for purposes of illustration, and accordingly are not to be construed as either delimiting or exclusionary.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences", 14 Ed., Merck Publishing Company, Eaton, Pa., 1965.

Approriate dosages, in any given instance, of course depend upon the nature and severity of the condition treated, the route of administration, and the species of mammal involved, including its size and any individual idosyncrasies which obtain.

A preferred method of preparing the compounds of this invention comprises contacting, in dichloromethane at 0° C., an acid of the formula

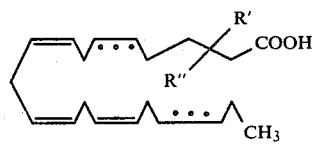

with N,N'-methanetetraylbiscyclohexanamine to produce the corresponding O-acylisourea

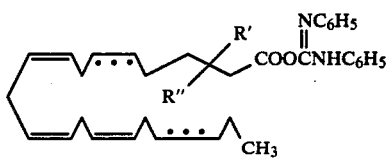

which in turn is contacted in dicloromethane with a phenol of the formula

ZOH

R', R", Z, and the dotted lines in the foregoing formulas retaining the meanings previously assigned. Alternatively, a 2-alkylated compound of this invention can be prepared by contacting, in tetrahydrofuran at −78° C. under nitrogen, an ester of the formula

with N-lithio-N-(1-methylethyl)cyclohexanamine to produce the corresponding ester enolate

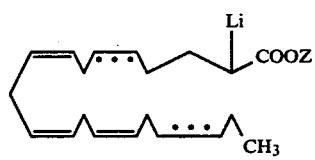

which is contacted in situ with an alkyl halide of the formula

R'I

R', Z, and the dotted lines being defined as before. The resultant 2-monoalkylated compound of the invention

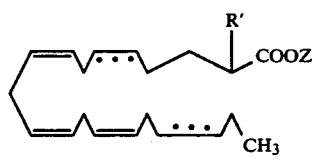

can be converted to a corresponding 2,2-dialkylated compound of the invention by contacting it in tetrahydrofuran at −78° C. under nitrogen with N-lithio-N-(1-methylethyl)cyclohexanamine, affording an ester enolate of the formula

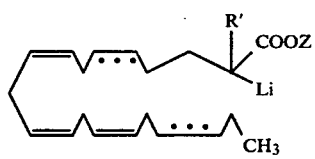

which in turn is contacted in situ with an alkyl halide of the formula

R"I

R" being defined as before.

Any of the 3-alkylated acids which serve as starting materials in the preferred method of preparing the esters of this invention disclosed above can be obtained by (1) contacting, in tetrahydrofuran at −78° C. under nitrogen, an appropriately-unsaturated ester of the formula

wherein the dotted lines are defined as before, with N-lithio-N-(1-methylethyl)cyclohexanamine; (2) contacting, in situ at −78° C. under nitrogen, the resultant ester enolate

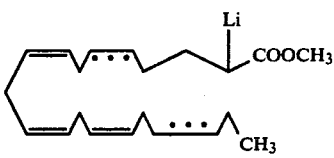

with diphenyl diselenide, whereby the substituent lithium is replaced by phenylseleno; (3) contacting the indicated 2-phenylseleno compound with sodium periodate in aqueous methanol; (4) contacting in anhydrous ether at −20° C., the α,β-unsaturated ester

thus obtained with a (dialkylcopper)lithium of the formula

R'$_2$CuLi wherein R' is defined as before, then contacting the resultant mixture with aqueous ammoniacal ammonium chloride at room temperature; and (5) saponifying the 3-alkylated ester

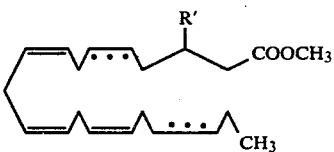

which eventuates by heating it with lithium iodide in 2,4,6-trimethylpyridine.

The following examples describe in detail compounds illustrative of the present invention and methods which have been devised for their preparation. It will be apparent to those skilled in the art that many modifications, both of materials and of methods, may be practiced without departing from the purpose and intent of the disclosure. Throughout the examples hereinafter set forth, temperatures are given in degrees centigrade and relative amounts of material in parts by weight, except as otherwise noted.

EXAMPLE 1

To a solution of 150 parts of 5Z,8Z,11Z,14Z-eicosatetraenoic acid in approximately 2700 parts of dichloromethane at 0° is slowly added a solution of 107 parts of N,N'-methanetetraylbiscyclohexanamine in approximately 800 parts of dichloromethane. The resultant mixture is stirred and allowed to warm to room temperature during 30 minutes, then filtered. To the filtrate is added 50 parts of phenol. The mixture thus obtained is stirred at room temperature overnight, then stripped of solvent by vacuum distillation under nitrogen. The distilland is phenyl 5Z,8Z,11Z,14Z-eicosatetraenoate, which is purified by chromatographing on silica gel, using hexane as the solvent. The product, a colorless liquid, has the formula

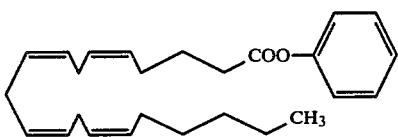

EXAMPLE 2

Substitution of 57 parts of 4-methylphenol for the phenol called for in Example 1 affords, by the procedure there detailed, 4-methylphenyl 5Z,8Z,11Z,14Z-eicosatetraenoate, having the formula

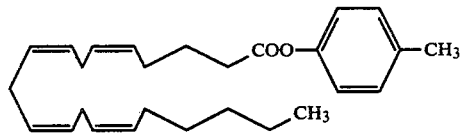

EXAMPLE 3

Substitution of 80 parts of 2-(1,1-dimethylethyl)-phenol for the phenol called for in Example 1 affords, by the procedure there detailed, 2-(1,1-dimethylethyl)-phenyl 5Z,8Z,11Z,14Z-eicosatetraenoate, having the formula

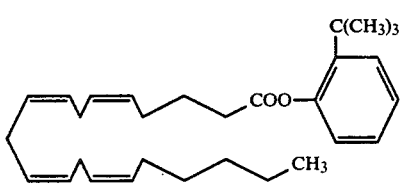

EXAMPLE 4

Substitution of 80 parts of 4-(1,1-dimethylethyl)-phenol for the phenol called for in Example 1 affords, by the procedure there detailed, 4-(1,1-dimethylethyl)-phenyl 5Z,8Z,11Z,14Z-eicosatetraenoate, having the formula

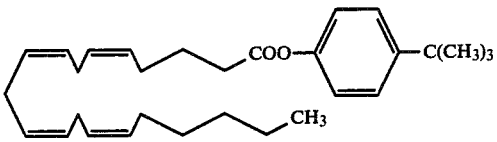

EXAMPLE 5

Substitution of 72 parts of 2,4,6-trimethylphenol for the phenol called for in Example 1 affords, by the procedure there detailed, 2,4,6-trhimethyphenyl 5Z,8Z,11Z,14Z-eicosatetraenoate, having the formula

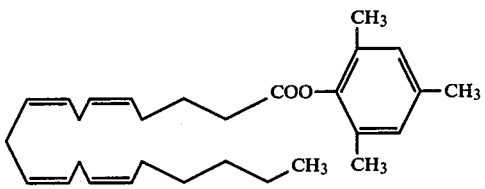

EXAMPLE 6

To a solution of 15 parts of N-(1-methylethyl)cyclohexanamine in 445 parts of tetrahydrofuran at −78° in a nitrogen atmosphere is slowly added, with stirring, a solution of 7 parts of butyllithium in 55 parts of hexane. The resultant mixture is stirred for 15 minutes at −78°, whereupon a solution of 44 parts of 4-(1,1-dimethylethyl)phenyl 5Z,8Z,11Z,14Z-eicosatetraenoate in 445 parts of of tetrahydrofuran is stirred in during 30 minutes at −78°. The mixture thus obtained is stirred at −78° for 30 minutes, at which point 15 parts of methyl iodide is introduced and the reactants then permitted to warm to room temperature, whereat solvent is removed by vacuum distillation. The distilland is extracted with hexane. The extract is washed with water, dried over anhydrous sodium sulfate, and stripped of solvent by vacuum distillation. The residue is 4-(1,1-dimethylethyl)phenyl 2-methyl-5Z,8Z,11Z,14Z-eicosatetraenoate, which is further purified by chromatographing on silica gel, using hexane as solvent. The product, a colorless liquid, has the formula

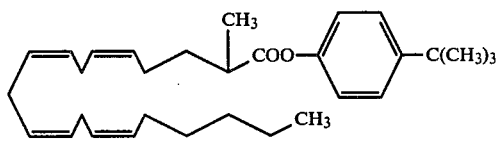

EXAMPLE 7

Substitution of 43 parts of 2,4,6-trimethylphenyl 4Z,8Z,11Z,14Z-eicosatetraenoate and 16 parts of ethyl iodide for the 4-(1,1-dimethylethyl)phenyl 5Z,8Z,11Z, 14Z-eicosatetraenoate and methyl iodide, respectively, called for in Example 6 affords, by the procedure there detailed, 2,4,6-trimethylphenyl 2-ethyl-5Z,8Z,11Z,14Z-eicosatetraenoate, having the formula

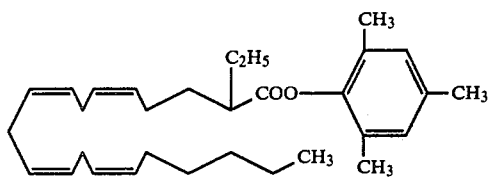

EXAMPLE 8

To a solution of 80 parts of N-(1-methylethyl)cyclohexanamine in 2000 parts of tetrahydrofuran at −78° in a nitrogen atmosphere is slowly added a solution of 32 parts of butyllithium in 250 parts of hexane. The resultant mixture is stirred for 15 minutes at −78°, whereupon a solution of 225 parts of 4-(1,1-dimethylethyl)phenyl 2-methyl-5Z,8Z,11Z, 14Z-eicosatetraenoate in 2000 parts of tetrahydrofuran is stirred during 30 minutes at −78°. The mixture thus obtained is stirred at −78° for 30 minutes, at which point 80 parts of methyl iodide is introduced and the reactants then permitted to warm to room temperature, whereat solvent is removed by vacuum distillation. The residue is 4-(1,1-dimethylethyl)phenyl 2,2-dimethyl-5Z,8Z,11Z,14Z-eicosatetraenoate, which is further purified by chromatographing on silica gel, using hexane as solvent. The product, a colorless liquid, has the formula

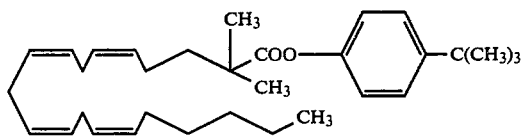

EXAMPLE 9

Substitution of 225 parts of 2,4,6-trimethylphenyl 2-ethyl-5Z,8Z,11Z,14Z-eicosatetraenoate and 87 parts of ethyl iodide for the 4-(1,1-dimethylethyl)phenyl 2-methyl-5Z,8Z,11Z,14Z-eicosatetraenoate and methyl iodide, respectively, called for in Example 8 affords, by the procedure there detailed, 2,4,6-trimethylphenyl 2,2-diethyl-5Z,8Z,11Z,14Z-eicosatetraenate. The product has the formula

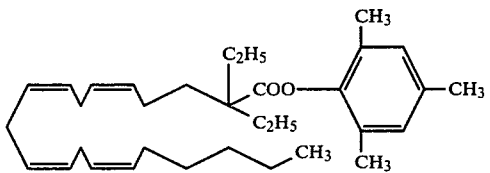

EXAMPLE 10

A. To a solution of 50 parts of N-(1-methylethyl)cyclohexanamine in approximately 900 parts of tetrahydrofuran at −78° in a nitrogen atmosphere is slowly added a solution of 23 parts of butyllithium in 180 parts of hexane. The resultant mixture is stirred for 15 minutes at −78°, whereupon a solution of 100 parts of methyl 5Z,8Z,11Z,14Z-eicosatetraenoate in 450 parts of tetrahydrofuran is stirred in during 30 minutes at −78°. The mixture thus obtained is stirred at −78° for 30 minutes, at which point a solution of 120 parts of diphenyl diselenide in 450 parts of tetrahydrofuran is introduced and the reactants then permitted to warm to room temperature and thereupon poured into 500 parts of a saturated aqueous solution of ammonium chloride. The mixture which eventuates is extracted with 1,1'-oxybisethane. The extract is acidified with 1% hydrochloric acid, then washed with water until the washings are neutral, whereupon the extract is dried over anhydrous sodium sulfate and finally stripped of solvent by vacuum distillation. The residue is methyl 2-phenylseleno-5Z,8Z,11Z,14Z-eicosatetraenoate, which is further purified by chromatographing on silica gel, using hexane as solvent. The product has the formula

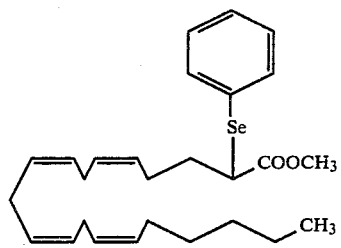

B. To a solution of 90 parts of methyl 2-phenylseleno-5Z,8Z,11Z,14Z-eicosatetraenoate in 800 parts of methanol is added, with stirring, a solution of 41 parts of sodium periodate in a mixture of 400 parts of methanol with 500 parts of water. Stirring is continued for 1 hour, whereupon the reaction mixture is filtered and the filtrate stripped of solvent by vacuum distillation. The residue is extracted with 1,1'-oxybisethane. The extract is washed with water, dried over anhydrous sodium sulfate, and stripped of solvent by vacuum distillation. The distilland is methyl 2E,5Z,8Z,11Z,14Z-eicosapentaenoate, which is further purified by chromatographing on silica gel, using hexane as solvent. The product has the formula

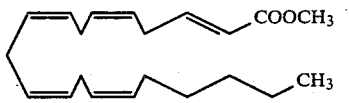

C. To a suspension of 31 parts of cuprous iodide in 350 parts of anhydrous 1,1'-oxybisethane at 31 20° is added, with stirring, a solution of 7 parts of methyllithium in 15 parts of anhydrous 1,1'-oxybisethane. Stirring at −20° is continued for 10 minutes, whereupon a solution of 50 parts of methyl 2E,5Z,8Z,11Z,14Z-eicosapentaenoate in 350 parts of anhydrous 1,1'-oxybisethane is slowly stirred in and stirring at −20° continued thereafter for a further 1 hour. At this point, 500 parts of a 10% solution of ammonium chloride in 10% ammonium hydroxide is mixed in; and the organic phase is separated and washed with a saturated aqueous solution of sodium thiosulfate and water until the washings are neutral. Solvent is then removed by vacuum distillation; and the residue is purified by chromatographing on silica gel, using hexane as solvent. The product thus isolated, a colorless liquid, is methyl 3-methyl-5Z,8Z,11Z,14Z-eicosatetraenoate, having the formula

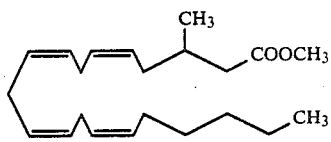

D. A mixture of 3 parts of methyl 3-methyl-5Z,8Z,11Z,14Z-eicosatetraenoate, 3 parts of lithium iodide, and 45 parts of 2,4,6-trimethylpyridine is heated at 170° for 3 hours, then cooled to room temperature and thereupon partitioned between 5% hydrochloric acid and 1,1'-oxybisethane. The ethereal phase is separated, washed with water until the washings are neutral, dried over calcium sulfate, and stripped of solvent by vacuum distillation. The residue is 3-methyl-5Z,8Z,11Z,14Z-eicosatetraenoic acid, having the formula

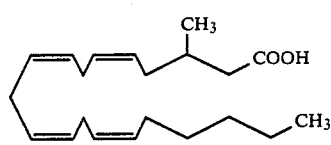

E. Substitution of 157 parts of 3-methyl-5Z,8Z,11Z,14Z-eicosatetraenoic acid and 80 parts of 4-(1,1-dimethylethyl)phenol for the 5Z,8Z,11Z,14Z-eicosatetraenoic acid the phenol, respectively, called for in Example 1 affords, by the procedure there detailed, 4-(1,1-dimethylethyl)phenyl 3-methyl-5Z,8Z,11Z,14Z-eicosatetraenoate, having the formul

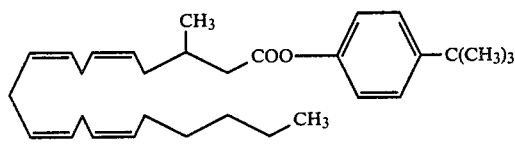

EXAMPLE 11

Substitution of 157 parts of 3-methyl-5Z,8Z,11Z,14Z-eicosaytetraenoic acid and 72 parts of 2,4,6-trimethylphenol for the 5Z,8Z,11Z,14Z-eicosatetraenoic acid and phenol, respectively, called for in Example 1 affords, by the procedure there detailed, 2,4,6-trimethylphenyl 3-methyl-5Z,8Z,11Z,14Z-eicosatetraenoate, having the formula

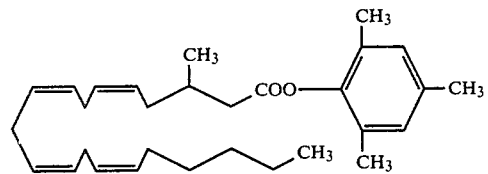

EXAMPLE 12

Substitution of 151 parts of 8Z,11Z,14Z-eicosatrienoic acid for the 5Z,8Z,11Z,14Z-eicosatetraenoic acid called for in Example 1 affords, by the procedure there detailed, phenyl 8Z,11Z,14Z-eicosatrienoate, having the formula

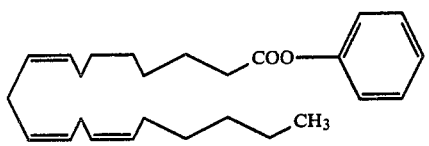

EXAMPLE 13

Substitution of 149 parts of 5Z,8Z,11Z,14Z,17Z-eicosapentaenoic acid for the 5Z,8Z,11Z,14Z-eicosatetraenoid acid called for in Example 1 affords, by the procedure there detailed, phenyl 5Z,8Z,11Z-14Z,17Z-eicosapentaenoate, having the formula

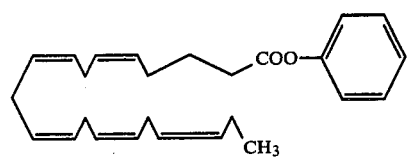

What is claim is:
1. A compound of the formula

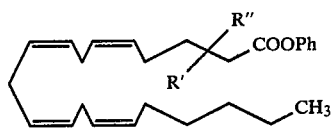

wherein R' represents hydrogen, 2-alkyl containing fewer than 3 carbons, or 3methyl; R" represents hydrogen or 2-alkyl containing fewer than 3 carbons except when R' represents 3-methyl, in which circumstance R" represents solely hydrogen; and Ph represents phenyl substituted by fewer than 4 alkyls each containing fewer than 5 carbons.

2. A compound according to claim 1 having the formula

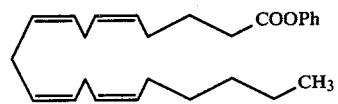

wherein Ph represents phenyl substituted by fewer than 4 alkyls each containing fewer than 5 carbons.

3. A compound according to claim 1 having the formula

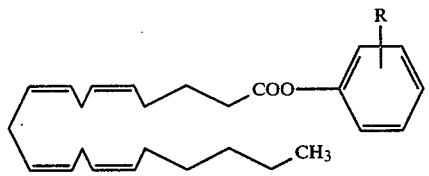

where R represents alkyl containing fewer than 5 carbons.

4. A compound according to claim 1 which is 4-(1,1-dimethylethyl)phenyl 5Z,8Z,11Z,14Z-eicosatetraenoate.

5. A compound according to claim 1 having the formula

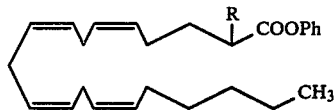

wherein R represents alkyl containing fewer than 3 carbons and Ph represents phenyl substituted by fewer than 4 alkyls each containing fewer than 5 carbons.

6. A compound according to claim 1 which is 4-(1,1-dimethylethyl)phenyl 2methyl-5Z,8Z,11Z,14Z-eicosatetraenoate.

7. A compound according to claim 1 having the formula

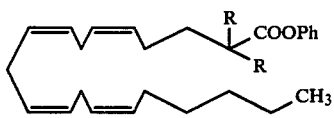

wherein R represents alkyl containing fewer than 3 carbons and Ph represents phenyl substituted by fewer than 4 alkyls each containing fewer than 5 carbons.

8. A compound according to claim 1 which is 4-(1,1-dimethylethyl)phenyl 2,2-dimethyl-5Z,8Z,11Z,14Z-eicosatetraenoate.

9. A compound according to claim 1 having the formula

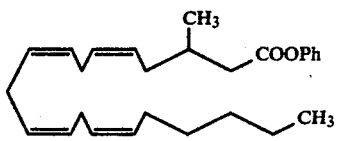

wherein Ph represents phenyl substituted by fewer than 4 alkyls each containing fewer than 5 carbons.

10. A compound according to claim 1 which is 4-(1,1-dimethylethyl)phenyl 3-methyl-5Z,8Z,11Z,14Z-eicosatetraenoate.

* * * * *